US005632739A

United States Patent [19]
Anderson et al.

[11] Patent Number: 5,632,739
[45] Date of Patent: May 27, 1997

[54] TWO-PULSE, LATERAL TISSUE ILLUMINATOR

[75] Inventors: Richard R. Anderson, Lexington; Joseph A. Grocela, Winchester, both of Mass.

[73] Assignee: The General Hospital Corporation, Mass.

[21] Appl. No.: 323,295

[22] Filed: Oct. 13, 1994

[51] Int. Cl.$^6$ .................................. A61N 5/06; H01S 3/09
[52] U.S. Cl. .................................................. 606/2; 606/15
[58] Field of Search .................................. 606/2, 10, 11, 606/12, 13, 14, 15, 16, 17, 18

[56] References Cited

U.S. PATENT DOCUMENTS

| | | | |
|---|---|---|---|
| 4,445,892 | 5/1984 | Hussein et al. | 604/101 |
| 4,519,390 | 5/1985 | Horne | 128/303.1 |
| 4,699,463 | 10/1987 | D'Amelio et al. | 350/96.26 |
| 4,785,815 | 11/1988 | Cohen | 128/642 |
| 4,819,632 | 4/1989 | Davies | 128/303.1 |
| 4,832,024 | 5/1989 | Boussignac et al. | 128/303.1 |
| 4,848,339 | 7/1989 | Rink et al. | 128/303.1 |
| 5,032,123 | 7/1991 | Katz et al. | 606/15 |
| 5,041,121 | 8/1991 | Wondrazek et al. | 606/128 |
| 5,116,227 | 5/1992 | Levy | 433/216 |
| 5,242,438 | 9/1993 | Saadatmanesh et al. | 606/17 |
| 5,321,715 | 6/1994 | Trost | 372/69 |
| 5,322,507 | 6/1994 | Costello et al. | 606/15 |
| 5,354,294 | 10/1994 | Chou | 606/17 |

FOREIGN PATENT DOCUMENTS

| | | | |
|---|---|---|---|
| 9113652 | 9/1991 | WIPO | 606/9 |
| WO93/12728 | 8/1993 | WIPO | A61B 17/36 |

*Primary Examiner*—Lee S. Cohen
*Assistant Examiner*—Sonya Harris-Ogugua
*Attorney, Agent, or Firm*—Fish & Richardson P.C.

[57] ABSTRACT

A two-pulse, lateral tissue illuminator in which a first pulse delivered by a first optical waveguide is used to irradiate a liquid-containing region to form a vapor bubble; a second pulse, delivered by a second optical waveguide, is then passed through the vapor bubble and used to incise a tissue of a patient. The illuminating device can be used to effectively deliver radiation to tissue positioned laterally relative to the axis of the delivery fibers, and allows a reduction in the attenuation of the radiation by the surrounding liquid.

16 Claims, 5 Drawing Sheets

TWO-PULSE, LATERAL TISSUE ILLUMINATOR

This invention was made with Government support under Contract N00014-91-C-0084 awarded by the Department of the Navy. The Government has certain rights in the invention.

FIELD OF THE INVENTION

This invention relates to a method for irradiating tissue, particularly tissue surrounded by a fluid environment.

BACKGROUND

Laser light sources are commonly used for medical applications, and are particularly effective for rapid, non-invasive surgical procedures. In one application, optical radiation from the light source is used to irradiate the tissue, where it is rapidly absorbed and converted into heat. The heated regions of tissue can be ablated in this manner, resulting in resection or incision of the tissue.

In a particular example, infrared lasers have recently been used during the transurethral resection of the prostate (the TURP procedure) as a way of treating benign prostatic hypertrophy. In this procedure, the infrared laser light is first coupled into a fiber optic waveguide, which is then fed through the urinary tract using a catheter. The fiber is positioned within the prostrate urethra and then used to irradiate and resect the hypertrophic region. The most common laser which has been used for this procedure is the Nd:YAG laser, which emits light at $\lambda=1.06$ microns. Light at this wavelength is not strongly absorbed, and thus deeply penetrates the tissue to produce only small amounts of ablation, while creating a wide region of coagulation necrosis. Alternatively, radiation from a holmium:YAG laser ($\lambda=2.1$ microns) is typically strongly absorbed by the tissue, and can be used to effectively ablate the irradiated region while leaving a relatively small region of coagulation necrosis.

Unfortunately, while infrared radiation is rapidly absorbed by water contained within the tissue, it is also absorbed by water surrounding the tissue, leading to an attenuation of the incising optical field. Absorption (and heating) of the water thus decreases the amount of radiation available for the surgical procedure, and may also lead to thermal lensing effects in the surrounding fluid which can reduce the accuracy of the procedure.

One technique used to reduce the absorption of infrared radiation in fluids, such as water, is the "Moses effect". Here, a first infrared optical pulse is used to irradiate a liquid region separating the tissue from, for example, the delivery end of an optical fiber. Absorption of the pulse leads to rapid heating of the fluid, creating a vapor bubble (i.e., an air or steam pocket surrounded by liquid) which expands outwardly in all directions. Once the bubble reaches a desirable size during a predetermined time period, a second laser pulse is delivered from the fiber and propagates through the bubble before reaching the tissue, thereby minimizing the absorption and attenuation by the surrounding fluid.

The amount of energy necessary to vaporize the liquid in order to create the vapor bubble is dependent on the absorbing properties of the liquid, and the carrier frequency, pulse duration, spot size, and pulse energy of the optical field. Other properties of the bubble, such as the volume and inflation lifetime, are additionally dependent on the optical properties of the fluid and the various parameters of the irradiating field. Typically, using water as the liquid and a Nd:YAG laser as the light source, bubbles having a volume of up to a few cubic centimeters can be formed during a time period of between 100 and 200 microseconds.

U.S. Pat. No. 5,321,715 (issued Jun. 14, 1994; assigned to Coherent, Inc.) describes the use of a pair of optical pulses to reduce the absorption effects of a liquid medium surrounding a tissue sample. In this device, a first pulse is used to generate the vapor bubble; a second pulse, emitted from the same fiber, propagates through the bubble to irradiate the tissue.

SUMMARY

In general, in one aspect, the invention provides a method of delivering a pulse of optical radiation through a liquid-containing region proximal to a tissue of a patient, and then to the tissue to produce ablation. The method includes the steps of generating a first and second optical pulse; the first optical pulse is of sufficient intensity to form a vapor bubble in the liquid-containing region, and the second pulse is of sufficient energy, after passing through the vapor bubble, to incise portions of the tissue. Once generated, the first optical pulse is delivered through a first optical waveguide and into the liquid-containing region proximal to the tissue so as to form the vapor bubble along a first pathway in the liquid-containing region. A predetermined time period is then allowed to elapse, resulting in expansion of the vapor bubble to an amount sufficient to displace portions of the liquid in the liquid-containing region along the first pathway. The second optical pulse is then delivered (a) through a distal end of a second optical waveguide and along a second pathway substantially orthogonal to the first pathway; (b) through portions of the vapor bubble; and (c) to the tissue of the patient. Delivery of the second pulse along the second pathway results in a reduction in attenuation of the pulse by the liquid, thereby increasing the amount of radiation available for incision of the tissue of the patient. By "substantially orthogonal", as used herein, is meant that the angle between the first and second pathways is between 70 and 110 degrees.

In preferred embodiments, the step of delivering the second pulse further includes, prior to step (b), the step of irradiating at least one reflective surface contained in a chamber enclosing a distal end of the second optical waveguide. The surface is irradiated at an angle so that the second pulse propagates out of the chamber and along a pathway substantially orthogonal to the pathway of the first pulse. In this case, the surface is preferably oriented at an angle of between 30 and 60 degrees, and most preferably at an angle of about 45 degrees.

In other preferred embodiments, the second waveguide is configured to irradiate a tissue positioned along the second pathway. Here, the tissue may be the prostate gland, in which case the first and second optical waveguides are preferably inserted into the urethra of the patient.

In other embodiments, the predetermined time period separating the first and second pulses allows the vapor bubble to expand along portions of the second pathway. Preferably, the time period allows the vapor bubble to expand so as to completely span the second pathway, and is in the range of between 100 and 1000 microseconds.

In still other embodiments, a single light source is used to generate the first and second optical pulses. The light source preferably emits irradiation in the infrared spectral region, and is selected from the group including Nd:YAG, Nd:YLF, Nd:YAP, Nd:YALO, Ho:YSGG, Ho:YAG, Ho:YLF, $CO_2$, Ti:sapphire, and infrared diode lasers. Most preferably, the laser is a Ho:YAG laser. Optical pulses produced by these light sources preferably have durations of between 100 and 1000 microseconds.

Alternatively, two separate light sources are used to generate the first and second optical pulses. In this case, it is preferred that the first light source emits a wavelength which is strongly absorbed by the liquid-containing region, and the second light source emits a wavelength which is strongly absorbed by the tissue region. Most preferably, the first and second light sources emit light in the infrared spectral region. Alternatively, the first light source emits light in the infrared spectral region, and the second light source emits light in the visible spectral region.

In another aspect, the invention provides an apparatus for delivering a pulse of optical radiation through a liquid-containing region proximal to a tissue of a patient, and then to the tissue so as to incise portions thereof. A first optical pulse, delivered using a first optical waveguide attached to the side of a chamber, is of sufficient intensity to form a vapor bubble in the liquid-containing region; a second optical pulse, delivered using a second optical waveguide enclosed by the chamber, is of sufficient energy to incise portions of the tissue after passing along a second pathway substantially orthogonal to the first pathway and through the vapor bubble.

In preferred embodiments, the distal tip of the second optical waveguide is cleaved so as to deliver the second optical pulse in a direction substantially orthogonal to the pathway of the first optical pulse. Alternatively, the distal tip of the second optical waveguide is cleaved orthogonally relative to the longitudinal axis of the waveguide, and the chamber further includes a partially reflective surface angled relative to the tip in order to reflect the second optical pulse out of the chamber and along a pathway substantially orthogonal to the pathway of the first pulse.

It yet another aspect of the invention, the chamber is omitted, and the first and second optical fibers are attached to each other. Preferably, in this case, the distal tip of the second optical waveguide is positioned below the distal tip of the first optical waveguide.

The inventions have many advantages. In particular, the illuminating device can non-invasively deliver radiation to tissues, while limiting blood loss and eliminating contact between the fiber and the tissue. In addition, the illuminating device can be used to effectively deliver radiation to tissue positioned laterally relative to the axis of the delivery fibers, while reducing attenuation of the radiation by the surrounding fluid. This method is particularly effective when implemented during VLAP/TURP procedures which involve guiding a waveguide-containing catheter through the urethra, and then irradiating the prostate tissue positioned laterally from the fiber (and urethra) axis. In addition, the use of two separate fibers allows the irradiating system to have maximum flexibility; separate light sources (emitting light at different wavelengths) may be tuned to the absorption bands of the tissue and the surrounding fluid, and then used for irradiation purposes. This ensures that both the vapor bubble and tissue ablation are achieved using the minimum amount of optical energy. Another major advantage is that the first pulse, which causes a vapor bubble to form, and the timing between the two pulses, can be used to regulate the depth of tissue ablation. The size of the vapor bubble when the second pulse arrives is chosen to set the depth of ablation.

DETAILED DESCRIPTION

Figure 1:
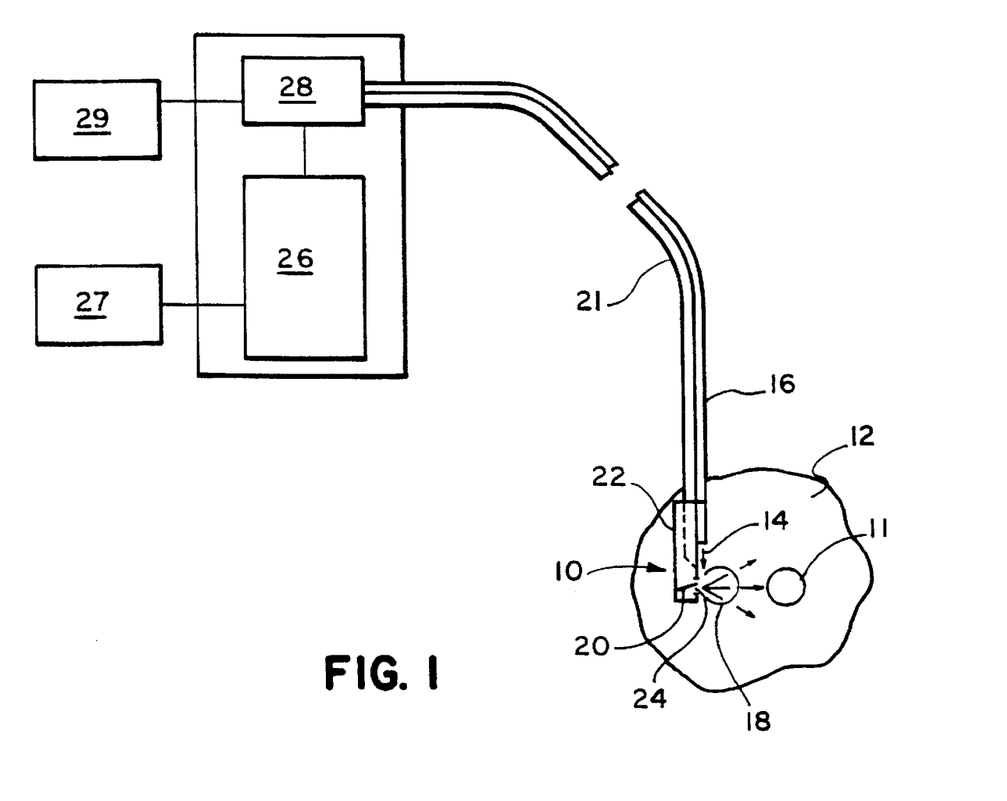
FIG. 1 is a schematic view of the two-pulse lateral tissue illuminator during irradiation of a tissue sample.
Figure 2:
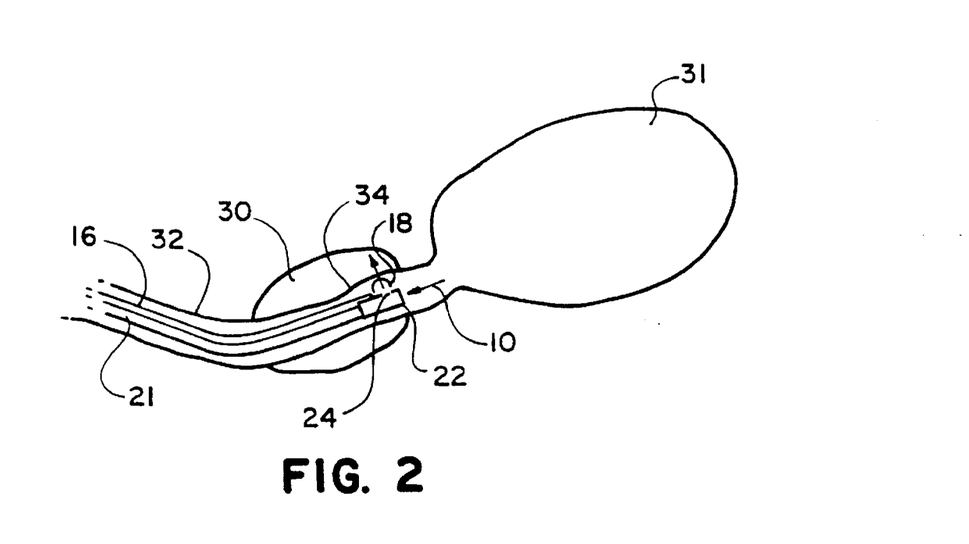
FIG. 2 is a side view of the tissue illuminator during irradiation of the prostate gland of a patient.

With reference to FIGS. 1 and 2, a tissue illuminator 10 designed to resect or incise a portion of a tissue sample 11 allows illumination of a portion of a fluid region 12 with a first optical field (indicated in the figure with the arrows 14) delivered through a first waveguide 16. The wavelength of the first optical field is chosen so that it is strongly absorbed by the fluid region or materials (e.g., proteins or blood cells) dispersed throughout the fluid region. Optical absorption results in a heating of the fluid region 12; when the temperature is raised from an ambient level to above the boiling point (i.e., 100 degrees centigrade for water) the heated portion of the fluid region is boiled, leading to vaporization and the creation of the vapor bubble region 18, composed primarily of vaporized water molecules (i.e., steam), which displaces portions of the surrounding fluid region 12.

A second optical field (indicated in the figure by the arrows 20) is then delivered through a second waveguide 21 to a hollow chamber 22 included in the tissue illuminator 10. The wavelength of the second optical field is chosen so that it is strongly absorbed by the tissue sample 11 within the liquid region 12. The distal end of the second waveguide 21 is encased in the chamber 22, and may be cleaved at an angle to allow the second optical field to reflect at an orthogonal angle. After being internally reflected at the fiber/air interface, the optical field propagates out through an opening 24 of the chamber 22, and into the newly created vapor bubble region 18. Alternatively, the fiber may be cleaved orthogonal to its central axis, and an interior wall of the chamber 22 may be angled so as to laterally direct the light out of the chamber 22. The optical pathway of the second optical field is determined by the angle of the cleaved waveguide and the geometry of the interior walls of the tube; preferably, light emerges along a pathway roughly orthogonal to that of the first optical field. Propagation of the second optical field through the vapor bubble region 18 results in a dramatic reduction in attenuation relative to propagation of the same field through a continuous fluid region. This is primarily because the second optical field, chosen to be absorbed by the tissue sample (composed primarily of water), is also strongly absorbed by the surrounding fluid region. Absorption by the gaseous vapor bubble is relatively low, allowing a large fraction of the second optical field to be delivered to the tissue sample 11.

The tissue illuminator is especially effective in illuminating tissue positioned in a way that direct illumination with the distal end of the second optical waveguide would be otherwise difficult or impossible. For example, during clinical use, the tissue illuminator 10 allows lateral illumination of tissue extending laterally from the central axes of the fibers and a lumen (e.g., a vein or urethra of the patient) through which the fibers are guided. Referring to FIG. 2, in a particular example, the transurethral resection of the prostate gland 30 located adjacent to the bladder 31 involves first guiding the first 16 and second 21 waveguides through the urethra 32 of the patient so that the tissue illuminator 10 is adjacent to the region of the prostate 30 which is to be illuminated. A first pulse is generated using a flashlamp-pumped holmium:YAG laser ($\lambda=2.1$ microns) and is delivered through the first waveguide, where it emerges and is absorbed by the urine present in the urethra 32. Heating of the urine or irrigation fluid in this manner results in vapor bubble formation, thereby displacing liquid present between the opening 24 of the chamber 22 and the prostate/urethra interface 34. This allows the second pulse, also at $\lambda=2.1$ microns, to be delivered across the interface 34 and into the prostate, where it is used for resection. In order to maximize the intensity of the resecting optical field, the second pulse is delayed with respect to the first pulse to allow maximum fluid displacement and minimal attenuation. Procedures done in this manner allow control over ablation depth, and result in excellent hemostasis (i.e., a reduction in bleeding), thereby reducing the patient's hospital stay.

Referring again to FIG. 1, an optical source 26, such as a single laser, driven by a laser control source 27, may be used to generate the first and second optical fields. Preferably, the optical field delivered to the fluid and tissue region are pulsed. In this case, the optical output from the laser may be pulsed using, for example, a time-dependent pumping source (i.e., a strobing flashlamp), diode laser pulses, or Q-switching electronics within the laser cavity. The duration of each pulse, and the spacing between the pulses, is determined using the laser control source. Alternatively, the laser may produce a continuous wave (cw) output, and may be modulated by an electro-optic modulating device 28, such as a Bragg cell, to produce the pulsed output. Here, the pulse durations and pulse spacings are determined by the modulator control source 29. In other embodiments, two separate lasers may be used to generate separate optical fields. This allows the wavelength, in addition to the pulse duration and pulse energy, to be tailored to create the desired effect, i.e., tissue ablation or fluid vaporization, in the eventual absorbing medium.

Preferably, the light source used to generate the first and second optical fields is an infrared light source, such as a diode, Nd:YAG, Nd:YLF, Nd:YAP, Nd:YALO, Holmium:YSGG, Ho:YAG, Ho:YLF, $CO_2$, thallium, or Ti:sapphire laser. These lasers produce an output having wavelengths in the range of 800 nm to 10 microns, some of which are strongly absorbed by water contained in the both the tissue and fluid regions. In the case where separate light sources are used to generate the first and second optical fields, the first light source is preferably one of the above-mentioned infrared light sources, and the second light source is chosen so that the emitted wavelength is strongly absorbed by the tissue sample. In this case, in addition to the infrared light sources, the light source may emit wavelengths in the ultraviolet (e.g., an excimer laser) or visible (e.g., a frequency doubled infrared laser, or an ion laser) frequency regimes.

Referring now to FIGS. 3A–3D, the first optical waveguide 16 of the tissue illuminator 10 is attached to the outer surface of the chamber 22 and is positioned above the chamber opening 24. The chamber 22 preferably encloses the distal portion of the second optical waveguide 21. Preferably, in all cases, the waveguide is an optical fiber or bundle of optical fibers, and is chosen so that the propagating optical field is minimally attenuated. The fibers preferably contain a silica or polymer core, and are surrounded by a protective polymer jacket. In order to deliver high-intensity optical fields, the fibers are preferably of large diameter (i.e., having diameters of between about 100 and 800 microns). Preferably, this diameter is chosen so that the fibers can effectively deliver the optical field while maintaining the flexibility necessary for conforming to the shape of the lumen into which they are positioned during the surgical procedure.

Figure 3A:
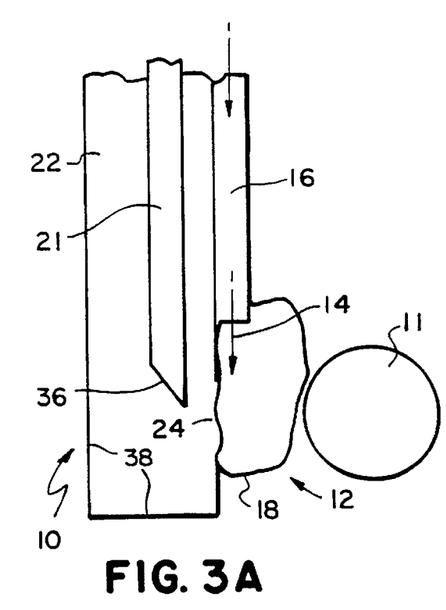
FIGS. 3A and 3C are side views of the tissue illuminator forming a vapor bubble in a liquid region.
Figure 3B:
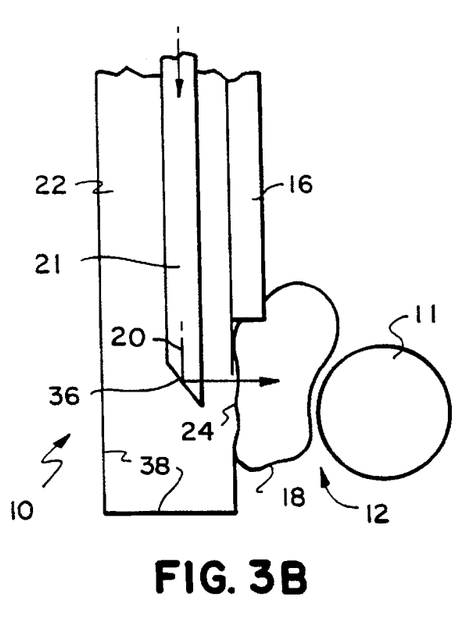
FIGS. 3B and 3D are side views of the tissue illuminator delivering radiation through the vapor bubble using, respectively, direct illumination from the optical fiber, and a single reflection off a chamber surface.

Referring now to FIGS. 3A and 3B, in one embodiment, the first optical pulse (indicated in FIG. 3A by the arrow 14) is delivered to the surrounding fluid region 12 to create a vapor bubble 18. After a predetermined time delay allowing for maximal fluid displacement by the vapor bubble 18, the second optical field (indicated in FIG. 3B by the arrow 20) is delivered to the distal tip 36 of the second waveguide 21, which is cleaved (preferably at an angle of 45 degrees) so that the field is emitted at an angle relative to the longitudinal axis of the waveguide 21. Preferably, in this embodiment, the distal tip 36 is cleaved so that the angle is between about 80–100 degrees. Once emitted from the fiber, the field propagates out of the chamber opening 24 and through the vapor bubble 18, and is delivered to the tissue sample 11 at an angle roughly orthogonal to the pathway of the first optical field.

Figure 3C:
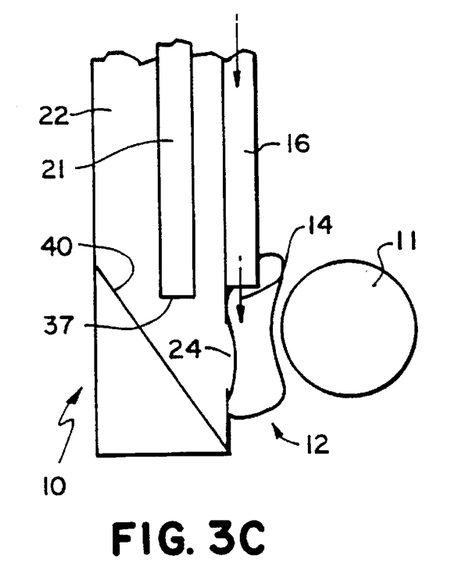
Figure 3D:
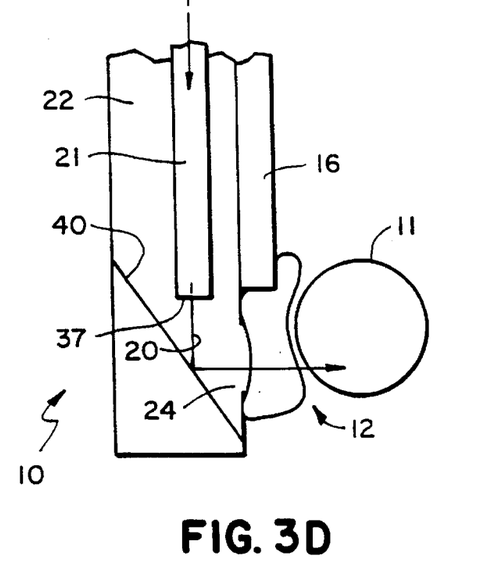

Referring now to FIGS. 3C and 3D, in another embodiment, a first optical field is used to create the vapor bubble, and a second optical field is emitted from the distal tip 37 of the fiber which is cleaved to be roughly orthogonal to the longitudinal axis of the fiber. In this case, a reflective surface 40 positioned at an angle of between about 30 and 60 degrees, and most preferably 45 degrees, allows the second optical field to be directly delivered through the vapor bubble 18 and to the tissue after a single reflection. In particular, this embodiment allows the angle of the second optical field (relative to both the vapor bubble and the extension of the waveguides 16, 21) to be accurately controlled. This is especially useful for surgical procedures where the waveguides are guided through a narrow lumen, and the tissue is positioned laterally from the lumen. The reflective surface may contain a highly reflective polished metal, or may be coated with a reflective material which, for example, may cause a diffuse reflection in order to provide a substantially uniform optical field of large area.

Figure 4:
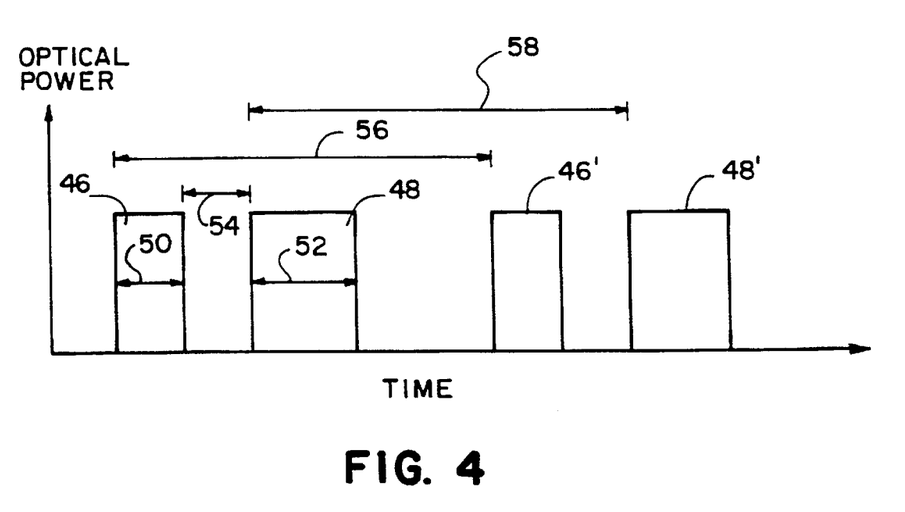
FIG. 4 is a schematic view of the timing sequence between the first and second pulses.

Referring now to FIG. 4, the time-dependent properties of the optical fields, i.e., the duration of and spacing between the first 46 and second 48 optical pulses, can be adjusted so as to maximize the amount of energy delivered to the tissue of interest. For example, the durations of the first 46 and second 48 optical pulses (indicated in the figure by arrows 50 and 52, respectively) can be adjusted so as to increase the amount of heat deposited in the liquid region, or in the tissue. In particular, the duration (i.e., power) of the first pulse 46 can be adjusted to vary the size, rate of expansion, and lifetime before collapse of the vapor bubble generated in the fluid region. Alternatively, the energy of the pulse can be adjusted to vary these properties. Preferably, for light at 2.1 microns, the time duration of the first pulse 46 is between about 1000 and 500 microseconds, and the pulse energy is between about 0.5 and 10 Joules/pulse. Typically, the collective size of the vapor bubbles produced with radiation of this magnitude is between about 0.5 and 6.0 $mm^3$, and the lifetime before collapse is about 100–400 microseconds.

The energy and time duration of the second pulse is adjusted according to the surgical procedure being performed. For example, the pulse energy or time duration may be increased to increase the depth of the heat-induced incision. During transurethral resection of the prostate, using 2.1 microns as the ablating wavelength, the energy of the pulse is typically between about 0.5 and 10 Joules/pulse, and the pulse duration can range from hundreds of microseconds to a few milliseconds. In other embodiments, the optical field used for resection or incision is not pulsed, i.e., it is cw.

In addition, because the vapor bubble size is time dependent, the time duration (indicated in the figure by the arrow 54) between the first 46 and second 48 optical pulses will determine the amount of fluid present in the pathway along which the second optical pulse 48 must propagate. Thus, this temporal separation partially determines the amount of radiation delivered to the tissue, and is dependent on the expansion rate of the bubble and the distance between the tissue illuminator and the target tissue. Preferably, the time duration separating the two pulses is chosen so that the second pulse 48 is emitted from the distal tip of the second fiber when the bubble size, and the corresponding amount of displaced fluid, is at a maximum. Typically, this separation is between about 50 and 600 microseconds, and is most preferably about 150 microseconds.

In addition, by modulating the output of the light source, the time-dependent intensity characteristics of the first and second pulses can be adjusted to achieve maximum delivery of radiation to the target tissue. For example, the first pulse may be modulated to have a triangular-shaped envelope; this results in a larger bubble formation rate when the maximal amount of optical energy (i.e., the "peak" of the triangular waveform) is delivered to the fluid.

During a surgical procedure, a single sequence of the first 46 and second 48 optical pulses may be used, or repetitive illumination of the tissue using multiple two-pulse sequences may be employed. In the latter case, the time periods separating the primary first pulse 46 from the secondary first pulse 46' (indicated in the figure by the arrow 56) and the primary second pulse 48 from the secondary second pulse 48' (indicated by the arrow 58) are determined by the repetition rate of the laser. This rate may be increased or decreased in order to vary the amount of irradiation delivered to the target tissue. When a single light source is used, the repetition rates for the first 46, 46' and second 48, 48' pulses is typically the same. Typically, this rate is long enough so that the vapor bubble completely collapses between laser shots, and is typically between about 10 and 1 kHz. Preferably, the repetition rate is between about 6 and 50 Hz. In the case where two separate light sources are used, the repetition rates of the primary and secondary first 46, 46' and second 48, 48' pulses can be independently varied.

EXAMPLES

The following examples are used to further describe the two-pulse lateral tissue illuminator.

Example 1—Pulse Timing

Referring now to FIGS. 5A–5B and 6A–6B, using the tissue illuminator according to the invention, the time dependence of the vapor bubble formation in water depends strongly on the time period separating the first and second pulses. In order to measure the bubble size as a function of time, the pulse energies ($E_{pulse}$) of the first and second pulses emitted from two separate holmium lasers (Coherent Inc., and Schwartz Electro-Optics, Inc.) were held constant, and the time period between the pulses was adjusted. Using a high-speed measuring technique incorporating a digitizing CCD camera and a pulsed dye laser as a flash source, it was possible to determine the temporal separation between the first and second pulse, and the time-dependent volume and expansion rate of the vapor bubble. In all cases, both the first and second pulses had a duration of between 100 and 300 microseconds, and zero time was arbitrarily set as the time in which the first laser was electronically triggered.

Figure 5A:
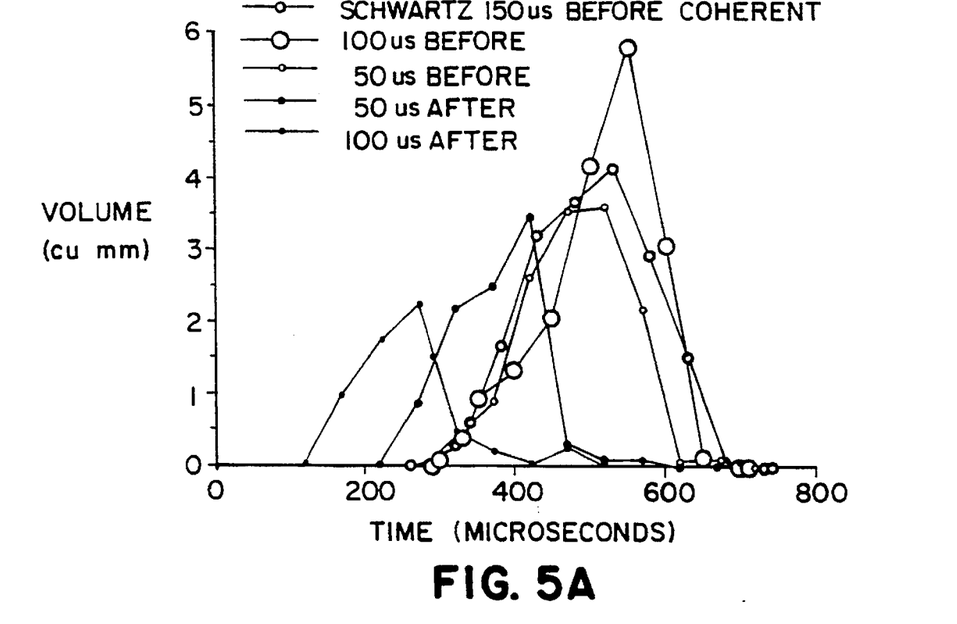
FIGS. 5A and 5B are plots showing the time-dependent formation of vapor bubbles in water.
Figure 6A:
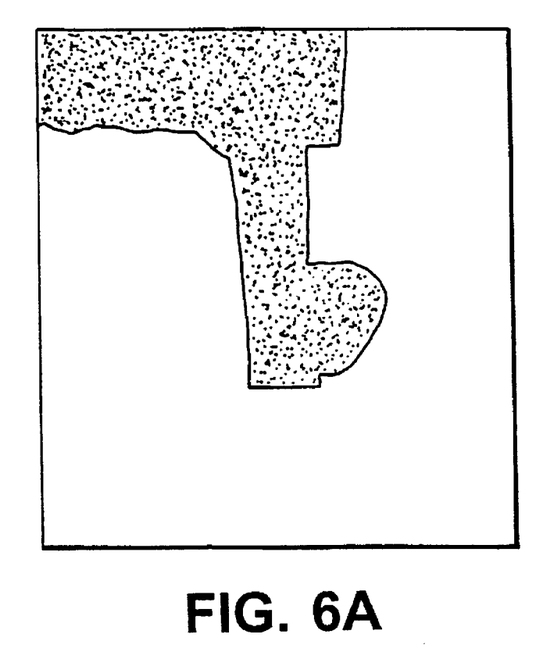
FIGS. 6A and 6B are images of vapor bubbles at maximum volumes using, respectively, the first pulse alone and the second pulse alone.
Figure 6B:
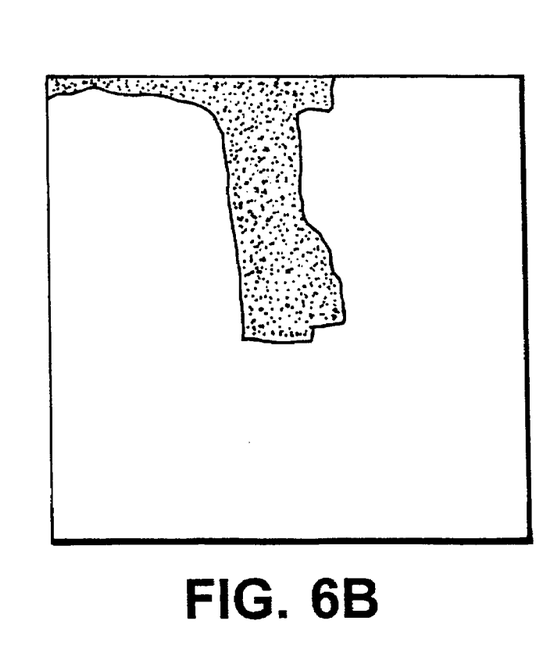

Referring now to FIG. 5A, by holding $E_{pulse,1}=0.8$ J/pulse, and $E_{pulse,2}=0.6$ J/pulse, the vapor bubble reached a maximum volume of about 5.5 mm$^3$ when the time separating the two pulses was about 100 microseconds. The time required for the vapor bubble to reach its peak volume was about 550 microseconds relative to zero time. The lifetime of the bubble (measured from initiation to collapse) was about 300 microseconds. A picture of the vapor bubble, taken with the high-speed CCD apparatus, is shown at a maximum size in FIG. 6A, and a slightly less than maximum size in FIG. 6B. In FIGS. 6A and 6B, respectively, the first and second pulses alone are used to generate the bubble. Both longer and shorter time delays (150 and 50 microseconds, respectively) resulted in lower-volume vapor bubbles (between about 3.5 and 4.0 mm$^3$ for both cases) which reached their maximum size after about 530 microseconds, and had lifetimes on the order of 300 microseconds.

Figure 5B:
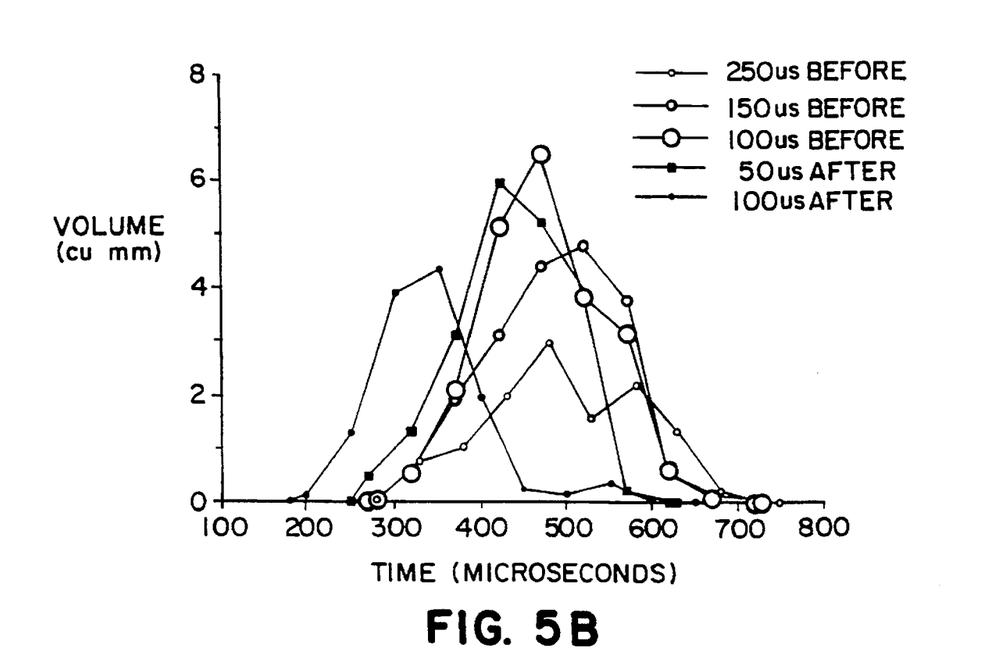

Referring now to FIG. 5B, by holding $E_{pulse,1}=0.8$ J/pulse, and $E_{pulse,2}=1.0$ J/pulse, the vapor bubble reaches a maximum size of about 6.1 mm$^3$ after about 480 microseconds relative to zero time; again, this maximum size is achieved when the first pulse irradiates the water region approximately 100 microseconds prior to the second pulse.

Example 2—In vivo use

The use of a two-pulse, lateral tissue illuminator was used to make surgical incisions in vivo in an anesthetized dog. During the procedure, a holmium laser (Schwartz Electro-Optics) was used to produce the first pulse for generating a vapor bubble, and emission from a second laser (Coherent, Inc.) was coupled into a chamber-enclosed fiber so as to laterally incise the bladder and prostate of the dog. As a control, the Schwartz laser alone was fired along a pathway tangential to the tissue to produce a shallow area of thermal injury. In a separate control, the Coherent laser alone was fired at a right angle relative to the prostate and bladder tissue, producing a shallow area of tissue ablation and a small amount of thermal damage. In the control experiments, there was a fair amount of bleeding from fine vessels in the irradiated tissue, which produced clouding of the irrigating fluid. This was done with the Coherent laser irradiating the tissue with 1.4 joules/pulse at a repetition rate of 8 pulses per second.

The dual-pulse experiment was performed by coupling the pulsed emission from the Schwartz laser (0.8 J/pulse) into the straight fiber to induce the vapor bubble. After a set delay of 200 microseconds, the pulsed emission from the Coherent laser (0.6 J/pulse) was delivered at a right angle relative to the pathway of the first pulse, through the induced vapor bubble, and to the tissue. The incision made during the two-pulse experiment was much deeper and wider than that made using the Coherent laser, alone. Additionally, the irrigation fluid remained clear while the prostate and bladder were incised, indicating excellent hemostasis in these tissues.

Other embodiments of the inventions are within the scope of the following claims.

What is claimed is:

1. A method of delivering a pulse of optical radiation through a liquid-containing region proximal to a tissue of a patient, and then to the tissue so as to irradiate portions thereof, the method comprising the steps of:

generating first and second optical pulses, wherein the first optical pulse is of sufficient intensity to form a vapor bubble in the liquid-containing region, and the second optical pulse is of sufficient energy, after passing through the vapor bubble, to irradiate portions of the tissue;

delivering the first optical pulse through a first optical waveguide and into the liquid-containing region so as to form the vapor bubble along a first pathway in the liquid-containing region;

allowing the vapor bubble to expand to displace some of the liquid in the liquid-containing region along the first pathway; and delivering the second optical pulse (a) through a distal end of a second optical waveguide and along a second pathway substantially orthogonal to the first pathway; (b) through a portion of the vapor bubble; and (c) to the tissue of the patient, said delivery along the second pathway reducing attenuation of the second optical pulse by the liquid, thereby increasing the amount of radiation available for irradiating the tissue.

2. The method of claim 1, wherein said step of delivering the second pulse further includes, prior to step (b), the step of irradiating a partially reflective surface contained in a chamber enclosing a distal end of the second optical waveguide, the surface being irradiated at an angle so that the second pulse propagates out of the chamber along a pathway substantially orthogonal to the pathway of the first pulse.

3. The method of claim 2, wherein the surface is irradiated so that the second pathway along which the second optical pulse is delivered is oriented at an angle of between 70 and 110 degrees relative to the longitudinal axis of the second optical waveguide.

4. The method of claim 3, wherein the angle is about 90 degrees.

5. The method of claim 2, wherein a tissue sample positioned along the second pathway is irradiated during delivery of the second optical pulse.

6. The method of claim 5, wherein the tissue sample is the prostate gland, and the first and second optical waveguides are inserted into the urethra of the patient.

7. The method of claim 1, wherein the predetermined time period allows the vapor bubble to expand along portions of the second pathway.

8. The method of claim 7, wherein the predetermined time period allows the vapor bubble to expand to completely span the second pathway.

9. The method of claim 1, wherein said predetermined time period is between 100 and 1000 microseconds.

10. The method of claim 1, wherein during said generating a single light source is used to generate the first and second optical pulses.

11. The method of claim 10, wherein the first and second optical pulses are in the infrared spectral region.

12. The method of claim 1, wherein the first and second optical pulses have durations of between 100 and 1000 microseconds.

13. The method of claim 12, wherein the first optical pulse is strongly absorbed by the liquid-containing region, and the second optical pulse is strongly absorbed by the tissue.

14. The method of claim 13, wherein the first and second optical pulses are in the infrared spectral region.

15. The method of claim 13, wherein the first optical pulse is in the infrared spectral region, and the second optical pulse is in the visible spectral region.

16. The method of claim 1, wherein during said generating two separate light sources are used to generate the first and second optical pulses.

* * * * *